United States Patent
Krapohl

(10) Patent No.: US 9,585,709 B2
(45) Date of Patent: Mar. 7, 2017

(54) SQUARE WAVE FOR VESSEL SEALING

(75) Inventor: James E. Krapohl, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 513 days.

(21) Appl. No.: 12/700,856

(22) Filed: Feb. 5, 2010

(65) Prior Publication Data

US 2011/0193608 A1    Aug. 11, 2011

(51) Int. Cl.
| | | |
|---|---|---|
| *H03K 3/00* | (2006.01) | |
| *A61B 18/12* | (2006.01) | |
| *A61B 18/14* | (2006.01) | |
| *A61B 18/00* | (2006.01) | |

(52) U.S. Cl.
CPC ...... *A61B 18/1206* (2013.01); *A61B 18/1477* (2013.01); *A61B 2018/0063* (2013.01); *A61B 2018/00589* (2013.01); *A61B 2018/00714* (2013.01); *A61B 2018/00779* (2013.01); *A61B 2018/00875* (2013.01); *A61B 2018/1425* (2013.01)

(58) Field of Classification Search
CPC .............................................. G11C 8/08–8/20
See application file for complete search history.

(56) References Cited

U.S. PATENT DOCUMENTS

| | | | |
|---|---|---|---|
| 3,897,787 A | 8/1975 | Ikuno et al. | |
| 4,016,886 A | 4/1977 | Doss et al. | |
| 4,034,762 A | 7/1977 | Cosens et al. | |
| 4,211,230 A | 7/1980 | Woltosz | |
| D263,020 S | 2/1982 | Rau, III | |
| 4,559,943 A | 12/1985 | Bowers | |
| D295,893 S | 5/1988 | Sharkany et al. | |
| D295,894 S | 5/1988 | Sharkany et al. | |
| 4,878,493 A | 11/1989 | Pasternak et al. | |
| D348,930 S | 7/1994 | Olson | |
| 5,396,194 A | 3/1995 | Williamson et al. | |
| D384,413 S | 9/1997 | Zlock et al. | |
| 5,777,519 A | 7/1998 | Simopoulos | |
| 5,781,048 A * | 7/1998 | Nakao et al. | ......... 327/157 |
| 5,964,759 A | 10/1999 | Yamanashi et al. | |
| D424,694 S | 5/2000 | Tetzlaff et al. | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 12/244,873, filed Oct. 3, 2008.

(Continued)

*Primary Examiner* — Sibin Chen

(57) ABSTRACT

A square wave generator suitable for use with an electrosurgical device is provided. The square wave generator includes a voltage source configured to output a waveform and a comparator operatively coupled to the voltage source and configured to output energy in the form of a square wave. The generator may also include at least one sensor configured to sense an operational parameter of the energy outputted from the comparator and to provide a sensor signal corresponding thereto and a controller adapted to receive the at least one sensor signal and in response thereto control the voltage source.

9 Claims, 4 Drawing Sheets

(56) References Cited

U.S. PATENT DOCUMENTS

| | | | |
|---|---|---|---|
| D425,201 S | 5/2000 | Tetzlaff et al. | |
| 6,059,781 A | 5/2000 | Yamanashi et al. | |
| 6,249,706 B1 | 6/2001 | Sobota et al. | |
| D449,886 S | 10/2001 | Tetzlaff et al. | |
| 6,301,506 B1 | 10/2001 | den Boer et al. | |
| D457,958 S | 5/2002 | Dycus et al. | |
| D457,959 S | 5/2002 | Tetzlaff et al. | |
| 6,385,265 B1* | 5/2002 | Duffy et al. | 375/374 |
| 6,575,968 B1 | 6/2003 | Eggers et al. | |
| D493,888 S | 8/2004 | Reschke | |
| D496,997 S | 10/2004 | Dycus et al. | |
| D499,181 S | 11/2004 | Dycus et al. | |
| D509,297 S | 9/2005 | Wells | |
| 7,041,096 B2 | 5/2006 | Malis et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,175,618 B2 | 2/2007 | Dabney et al. | |
| D541,418 S | 4/2007 | Schechter et al. | |
| D541,938 S | 5/2007 | Kerr et al. | |
| 7,254,433 B2* | 8/2007 | Diab et al. | 600/336 |
| 7,300,437 B2 | 11/2007 | Pozzato | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,432,764 B2* | 10/2008 | Oppelt | H03F 1/34 330/265 |
| 7,839,674 B2* | 11/2010 | Lowrey et al. | 365/163 |
| 7,898,288 B2* | 3/2011 | Wong | 326/30 |
| 2002/0029036 A1 | 3/2002 | Goble et al. | |
| 2003/0181898 A1* | 9/2003 | Bowers | A61B 18/1206 606/34 |
| 2004/0172017 A1* | 9/2004 | Marion et al. | 606/37 |
| 2005/0015125 A1 | 1/2005 | Mioduski | |
| 2007/0279019 A1* | 12/2007 | Wilson | 323/255 |
| 2008/0234674 A1* | 9/2008 | McClurken et al. | 606/50 |
| 2009/0118802 A1 | 5/2009 | Mioduski | |
| 2010/0174283 A1* | 7/2010 | McNall, III | A61B 18/1485 606/45 |
| 2010/0253663 A1* | 10/2010 | Ogata | 345/208 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 20 2007 009317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2004083797 | 9/2004 |
| WO | WO 2005/110264 | 11/2005 |

OTHER PUBLICATIONS

U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20, 2010.
U.S. Appl. No. 12/692,414, filed Jan. 22, 2010.
U.S. Appl. No. 12/692,810, filed Jan. 25, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.

(56) References Cited

OTHER PUBLICATIONS

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.

(56) References Cited

OTHER PUBLICATIONS

Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11153503.5 dated Feb. 28, 2012.

* cited by examiner

SQUARE WAVE FOR VESSEL SEALING

BACKGROUND

1. Technical Field

The present disclosure relates to systems for providing energy to biological tissue and, more particularly, to an apparatus that utilizes square waves to deliver energy to biological tissue.

2. Background of the Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is most commonly a monopolar procedure that is particularly useful in the field of cancer treatment, where one or more RF ablation needle electrodes (usually having elongated cylindrical geometry) are inserted into a living body and placed in the tumor region of an affected organ. A typical form of such needle electrodes incorporates an insulated sheath from which an exposed (uninsulated) tip extends. When RF energy is provided between the return electrode and the inserted ablation electrode, RF current flows from the needle electrode through the body. Typically, the current density is very high near the tip of the needle electrode, which tends to heat and destroy surrounding issue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned immediately adjacent the electrodes. When the electrodes are sufficiently separated from one another, the electrical circuit is open and thus inadvertent contact with body tissue with either of the separated electrodes does not cause current to flow.

Typically, sinusoidal waveforms are used to deliver energy for a desired tissue effect in electrosurgical and vessel sealing applications. Creating sinusoidal waveforms requires the use of low harmonic content linear drive or resonant switching amplifier topologies. However, linear drive electronics, which use linear components such as resistors, capacitors and inductors, tend to be inefficient due to the power loss caused by such linear components. With regard to resonant amplifier topologies, such topologies require large resonant components to shape the output waveform.

Further, in order to achieve excellent tissue sealing performance, it is important to monitor the impedance of the tissue to which energy is being applied. The impedance is calculated by measuring the root mean square (RMS) voltage and current of the radio frequency (RF) energy output to calculate the tissue impedance. However, with sinusoidal waveforms, complicated sensing hardware and/or signal processing is required to accurately calculate RMS voltage and/or current. Further, sinusoidal waveforms tend to have a peak voltage that 1.414 times the RMS voltage of the waveform. The higher peak voltage may have a negative impact on certain tissue treatments.

SUMMARY

The present disclosure provides a square wave generator suitable for use with an electrosurgical device in an embodiment of the present disclosure. The square wave generator includes a voltage source configured to output a waveform and a comparator operatively coupled to the voltage source and configured to output energy in the form of a square wave. The generator may also include at least one sensor configured to sense an operational parameter of the energy outputted from the comparator and to provide a sensor signal corresponding thereto, and a controller adapted to receive the at least one sensor signal and in response thereto control the voltage source.

The square wave generator may also include a positive high voltage direct current source coupled to the comparator and a negative high voltage direct current source coupled to the comparator. The controller may control the output of the positive high voltage direct current source and the negative high voltage direct current source in response to the at least one sensor signal to control the output of the square wave generator.

The operational parameter sensed by the circuit may be peak voltage or current.

In another embodiment of the present disclosure, a square wave generator suitable for use with an electrosurgical device is provided. The square wave generator includes a waveform synthesizer configured to output a waveform and an amplifier operatively coupled to the waveform synthesizer and configured to output energy in the form of a square wave. The generator may also include at least one sensor configured to sense an operational parameter of the energy outputted from the comparator and to provide a sensor signal corresponding thereto, and a controller adapted to receive the at least one sensor signal and in response thereto control the voltage source.

The square wave generator may also include a positive high voltage direct current source coupled to the comparator and a negative high voltage direct current source coupled to the comparator. The controller may control the output of the positive high voltage direct current source and the negative high voltage direct current source in response to the at least one sensor signal to control the output of the square wave generator.

The operational parameter sensed by the circuit may be peak voltage or current.

The amplifier may include at least two gain elements arranged in a push-pull configuration. The at least two gain elements are selected from the group consisting of bipolar transistors, field-effect transistors, and laterally diffused metal oxide semiconductors.

The square wave generator may also have a gain stage coupled between the waveform synthesizer and the amplifier. The gain stage may include a transformer.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
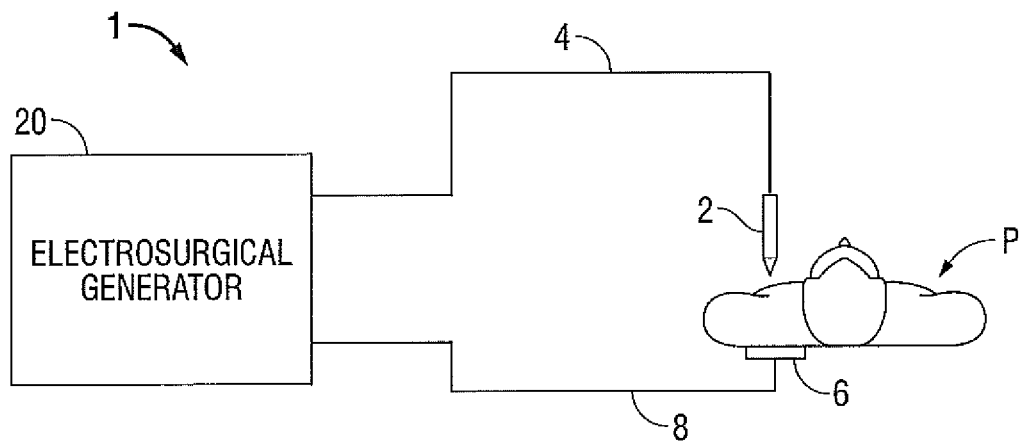
FIGS. 1A-1B are schematic block diagrams of an electrosurgical system according to the present disclosure for use with various instrument types.

Particular embodiments of the present disclosure are described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The generator according to the present disclosure can perform ablation, monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via a supply line 4, which is connected to an active terminal (FIG. 2) of the generator 20, allowing the instrument 2 to coagulate, ablate and/or otherwise treat tissue. The energy is returned to the generator 20 through a return electrode 6 via a return line 8 at a return terminal (FIG. 2) of the generator 20. The active terminal and the return terminal are connectors configured to interface with plugs (not explicitly shown) of the instrument 2 and the return electrode 6, which are disposed at the ends of the supply line 4 and the return line 8, respectively.

The system 1 may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage. In one embodiment, the active electrode 6 may be used to operate in a liquid environment, wherein the tissue is submerged in an electrolyte solution.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 1B:
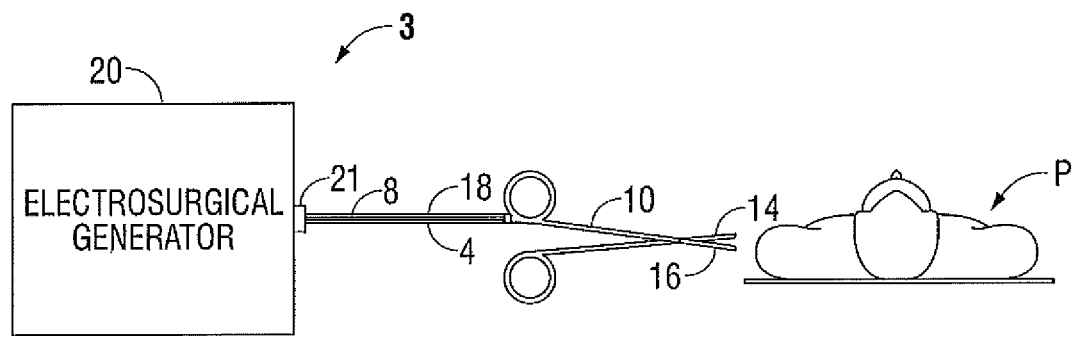

FIG. 1B is a schematic illustration of a bipolar electrosurgical system 3 according to the present disclosure. The system 3 includes a bipolar electrosurgical forceps 10 having one or more electrodes for treating tissue of a patient P. The electrosurgical forceps 10 include opposing jaw members having an active electrode 14 and a return electrode 16, respectively, disposed therein. The active electrode 14 and the return electrode 16 are connected to the generator 20 through cable 18, which includes the supply and return lines 4, 8 coupled to the active and return terminals 112 and 114, respectively. The electrosurgical forceps 10 are coupled to the generator 20 at a connector 21 having connections to the active and return terminals (e.g., pins) via a plug disposed at the end of the cable 18, wherein the plug includes contacts from the supply and return lines 4, 8.

Figure 2:
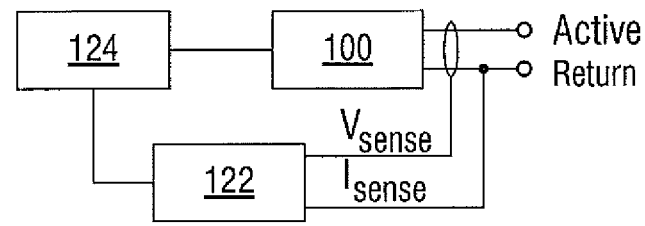
FIG. 2 is a schematic block diagram of a generator according to an embodiment of the present disclosure.

FIG. 2 is a schematic block diagram of the generator 20 shown in FIG. 1 for use with an electrosurgical system according to an embodiment of the present disclosure. As shown in FIG. 2, generator 20 includes a square wave generator 100, active terminal 112, return terminal 114, sensor 122 and controller 124. Square wave generator 100 is operatively coupled to active terminal 112 to provide electrosurgical energy in the form of a square wave to an electrosurgical instrument. In particular, the active terminal 112 generates either continuous or pulsed square waveforms of high RF energy. The active terminal 112 is configured to generate a plurality of waveforms having various duty cycles, peak voltages, crest factors, and other suitable parameters. Certain types of waveforms are suitable for specific electrosurgical modes. For instance, the active terminal 112 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The generator 20 may implement a closed and/or open loop control schemes that include a sensor circuit 122 having a plurality of sensors measuring a variety of tissue and energy properties (e.g., tissue impedance, tissue temperature, output current and/or voltage, etc.), and providing feedback to the controller 124. A current sensor can be disposed at either the active or return current path or both and voltage can be sensed at the active electrode(s). The controller 124 then transmits appropriate signals to the square wave generator 100, which then adjusts AC or DC power supply, respectively, by using a maximum allowable energy that varies according to the selected mode. The controller 124 also receives input signals from the input controls of the generator 20 or the instrument 2. The controller 124 utilizes the input signals to adjust power output by the generator 20 and/or performs other control functions thereon.

When electrosurgical energy is applied to tissue, the impedance of the tissue changes. The sensor circuit 122 measures the electrical current (I) and voltage (V) supplied by the active terminal 112 in real time to characterize the electrosurgical process during application of electrosurgical energy to tissue. This allows for the measured electrical properties to be used as dynamic input control variables to achieve feedback control. The current and voltage values may also be used to derive other electrical parameters, such as power (P=V*I) and impedance (Z=V/I). The sensor circuit 122 also measures properties of the current and voltage waveforms and determines the shape thereof.

The controller 124 includes a microprocessor operably connected to a memory, which may be volatile type memory (e.g., RAM) and/or non-volatile type memory (e.g., flash media, disk media, etc.). The controller 124 includes an output port that is operably connected to the square wave generator 100 allowing the controller 124 to control the output of the generator 20 according to either open and/or closed control loop schemes. Those skilled in the art will appreciate that the microprocessor may be substituted by any logic processor or analog circuitry (e.g., control circuit) adapted to perform the calculations discussed herein.

Because the output of generator 20 is a square wave, the RMS voltage and current is equal to the peak value of the square wave. As such, generator 20 does not need complicated sense hardware and/or signal processing that is usually required to accurately calculate RMS voltage and/or current for sinusoidal waveforms. Therefore, generator 20 has fewer components than the typical electrosurgical generator. Further, because the output of generator 20 is a square wave, generator 20 does not need large resonant components to shape the square wave.

Additionally, square wave generators are more efficient and can be made smaller than the typical electrosurgical generator in both the amplifier and sensor sections. Accordingly, a generator according to the above described embodiment may be incorporated into a portable handheld surgical device capable of being powered by a battery, battery pack or other portable power supply.

Figure 3:
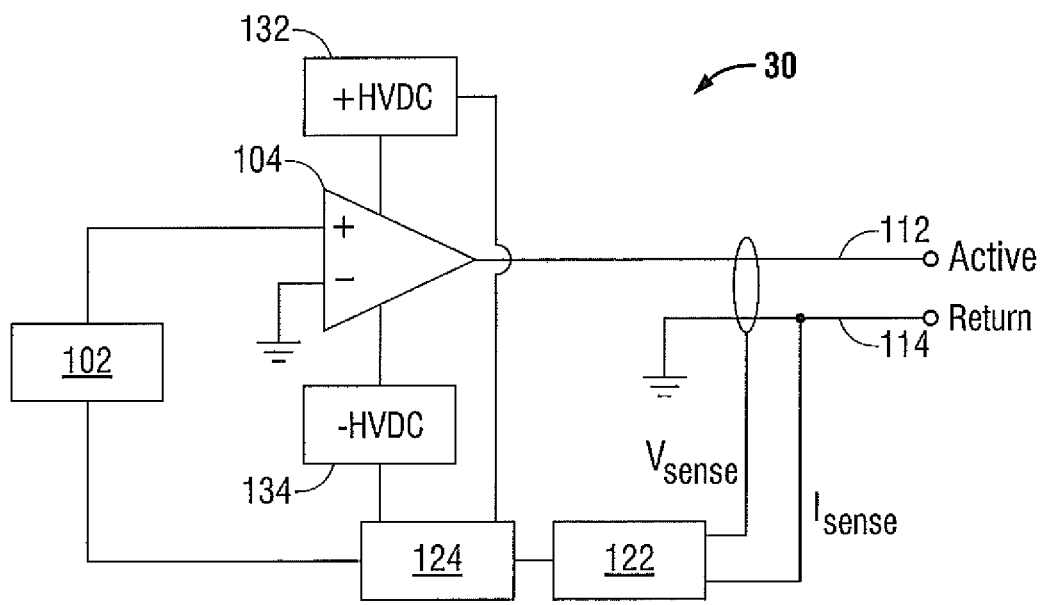
FIG. 3 is a schematic diagram of a generator according to another embodiment of the present disclosure.

FIG. 3 is a schematic illustration of a generator 30 for use with an electrosurgical system according to another embodiment of the present disclosure. As shown in FIG. 3, generator 30 has a voltage source 102 that generates an output voltage that is transmitted to comparator 104. The output voltage may be in the form of a sine wave, saw tooth wave or square wave. The output voltage is compared to a reference voltage at the negative input of comparator 104. Although FIG. 3 shows the reference voltage as ground any other voltage may be used as a reference voltage.

Comparator 104 is supplied with a positive high voltage direct current (+HVDC) source 132 and a negative high voltage direct current (−HVDC) source 134. As such, when the output voltage from voltage source 102 is positive, the output of comparator 104 is +HVDC and when the output voltage from voltage source 102 is negative, the output of comparator 104 is −HVDC. The comparator output is coupled to the active terminal 112 and provides energy in the form of a square wave to the electrosurgical instrument.

Generator 30 may implement a closed and/or open loop control schemes that include a sensor circuit 122 having a plurality of sensors measuring a variety of tissue and energy properties (e.g., tissue impedance, tissue temperature, output current and/or voltage, etc.), and providing feedback to the controller 124. A current sensor can be disposed at either the active or return current path or both and voltage can be sensed at the active electrode(s). The controller 124 then transmits appropriate signals to the voltage source 102, +HVDC source 132 and/or −HVDC source 134, which then adjusts AC or DC power supply, respectively, by using a maximum allowable energy that varies according to the selected mode. The controller 124 also receives input signals from the input controls of the generator 20 or the instrument 2. The controller 124 utilizes the input signals to adjust power output by the generator 20 and/or performs other control functions thereon.

Figure 4:
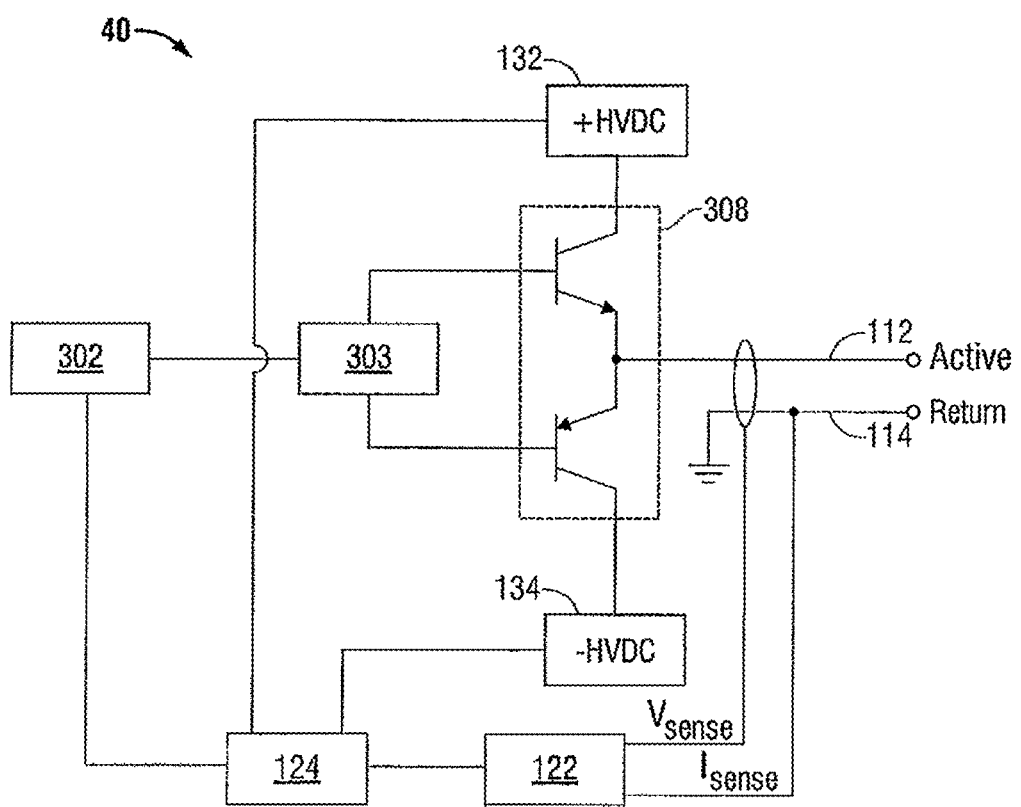
FIG. 4 is a schematic diagram of a generator according to another embodiment of the present disclosure.

FIG. 4 is a schematic illustration of a generator 40 according to another embodiment of the present disclosure. As shown in FIG. 4, generator 40 includes a waveform synthesizer 302 that generates waveforms having various duty cycles, peak voltages, crest factors, and other suitable parameters based on a selected mode for the electrosurgical device. Waveform synthesizer 302 may include a pulse width modulated (PWM) controller that generates a PWM signal.

The output of waveform synthesizer 302 is fed into voltage gain stage 303. Voltage gain stage 303 amplifies the input voltage and provides the amplified voltage as an output to a class A/B amplifier 308. Voltage gain stage 303 may include a transformer to provide patient isolation between the waveform synthesizer 302 and the patient. Voltage gain stage 303 may also include a bias circuit that can be controlled by controller 124 to provide a bias voltage for the class A/B amplifier 308. The combined power amplifier formed by 303 and 308 may be run open-loop or closed-loop.

Amplifier 308 may include two transistors in a push-pull configuration and may be a part of the voltage gain stage 303 or be discrete components. The two transistors in amplifier 308 may be bipolar transistors, field-effect transistors or laterally diffused metal oxide semiconductors. When a positive voltage is applied to the base of Q1, a high positive voltage from +HVDC source 132 is supplied to the active terminal 112. When a negative voltage is applied to the base of Q2, a high negative voltage from −HVDC source 134 is supplied to active terminal 112.

Generator 40 also includes a sensor circuit 122 that measures the electrical current (I) and voltage (V) supplied by the active terminal 112 in real time to characterize the electrosurgical process for a predetermined sampling period. Sensor circuit 122 provides a feedback signal to controller 124. Controller 124 analyzes the feedback signal and controls the output of the waveform synthesizer 302, +HVDC source 132 and −HVDC source 132 based on the feedback signal.

Figure 5:
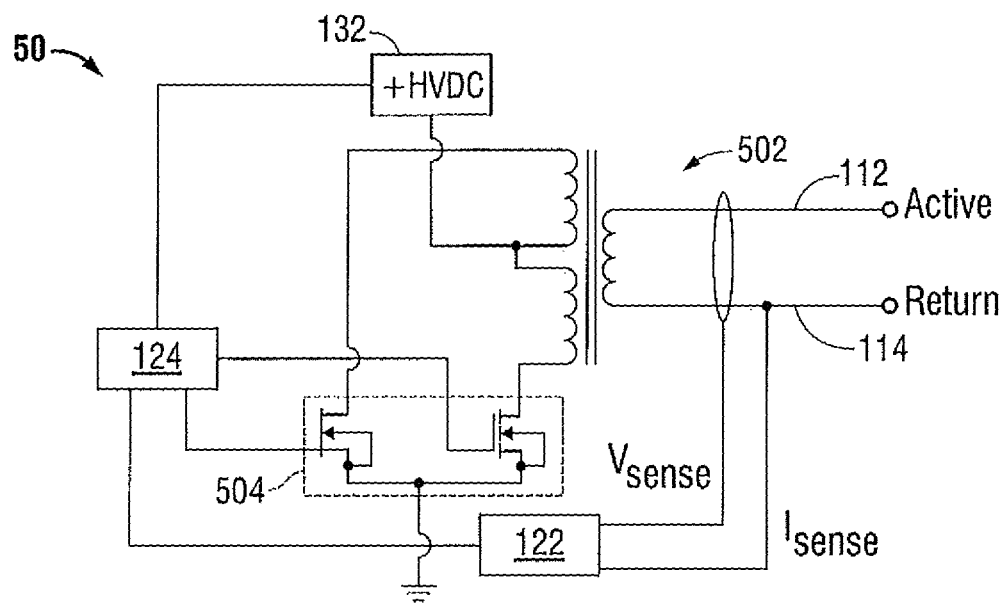
FIG. 5 is a schematic diagram of a generator according to another embodiment of the present disclosure.

FIG. 5 is a schematic illustration of a generator 50 according to another embodiment of the present disclosure. As shown in FIG. 5, generator 50 includes switching amplifier 504 in a push-pull configuration that generates waveforms having various duty cycles, peak voltages, crest factors, and other suitable parameters based on a selected mode for the electrosurgical device. Switching amplifier 504 may include two transistors in a push-pull configuration. The two transistors in switching amplifier 504 may be bipolar transistors, field-effect transistors or laterally diffused metal oxide semiconductors. The output of switching amplifier 504 is fed into transformer 502. Transformer 502 receives the input voltage and provides an output voltage to active terminal 112.

Generator 50 also includes a sensor circuit 122 that measures the electrical current (I) and voltage (V) supplied by the active terminal 112 in real time to characterize the electrosurgical process for a predetermined sampling period. Sensor circuit 122 provides a feedback signal to controller 124. Controller 124 analyzes the feedback signal and controls the output of the switching amplifier 504 based on the feedback signal.

Figure 6:
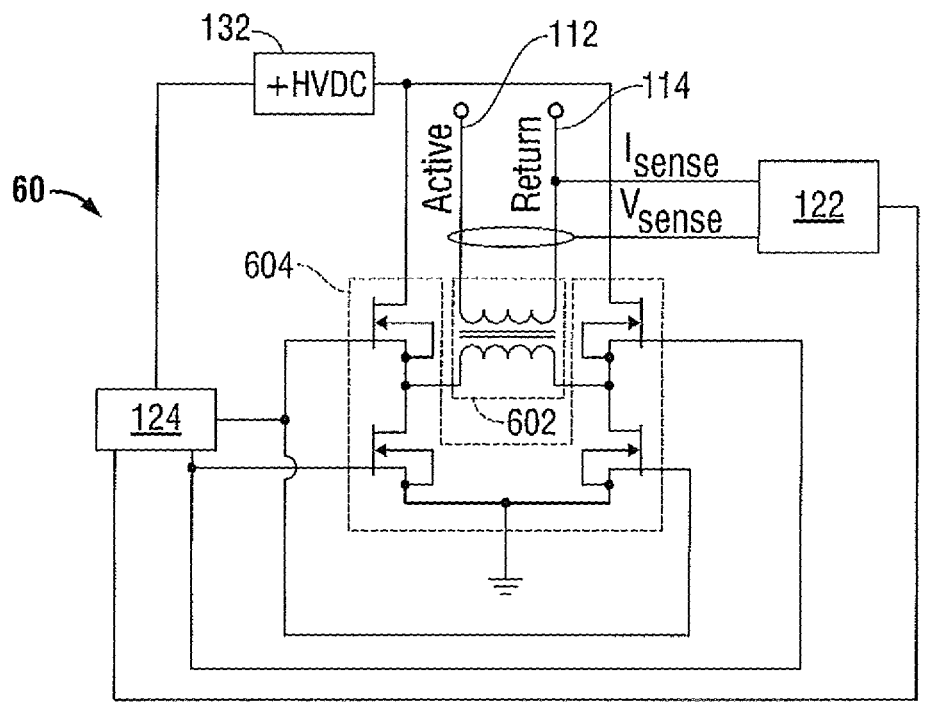
FIG. 6 is a schematic diagram of a generator according to another embodiment of the present disclosure.

FIG. 6 is a schematic illustration of a generator 60 according to another embodiment of the present disclosure. As shown in FIG. 6, generator 60 includes switching amplifier 604 in a full-bridge configuration that generates waveforms having various duty cycles, peak voltages, crest factors, and other suitable parameters based on a selected mode for the electrosurgical device. Switching amplifier 604 may include four transistors that may be bipolar transistors, field-effect transistors or laterally diffused metal oxide semiconductors. The output of switching amplifier 604 is fed into transformer 602. Transformer 602 receives the input voltage and provides an output voltage to active terminal 112.

Generator 60 also includes a sensor circuit 122 that measures the electrical current (I) and voltage (V) supplied by the active terminal 112 in real time to characterize the electrosurgical process for a predetermined sampling period. Sensor circuit 122 provides a feedback signal to controller 124. Controller 124 analyzes the feedback signal and controls the output of the switching amplifier 604 based on the feedback signal.

The generators described above with regard to FIGS. 2-6 include suitable input controls (e.g., buttons, activators, switches, touch screen, etc.) for controlling the generator. In addition, the generator may include one or more display screens for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). The instrument 2 may also include a plurality of input controls that may be redundant with certain input controls of the generator. Placing the input controls at the instrument 2 allows for easier and faster modification of RF energy parameters during the surgical procedure without requiring interaction with the generator.

The generator may include a plurality of connectors to accommodate various types of electrosurgical instruments (e.g., instrument 2, electrosurgical forceps 10, etc.). Further, the generator may operate in monopolar or bipolar modes by including a switching mechanism (e.g., relays) to switch the supply of RF energy between the connectors, such that, for instance, when the instrument 2 is connected to the generator, only the monopolar plug receives RF energy.

Using square waves for treating tissue has many advantages over using sinusoidal waves. Square waves generators do not require additional resonant components to shape the waveform. Accordingly, a generator using a square wave output topology has a smaller implementation and a smaller component count than a generator that outputs a sinusoidal wave. Further, when using sinusoidal waves, complicated sensing hardware and/or signal processing may be required to calculate the RMS voltage and/or current. For example, to calculate the RMS voltage of a sinusoidal wave, multiple samples of the voltage waveform have to be measured and then applied to complicated digital signal processing algorithms to obtain the RMS voltage value. On the other hand, with a square wave output, a single sample may be used to obtain the RMS voltage value because the peak voltage value is equal to RMS voltage in a square wave. The simplified sensing method associated with square wave outputs reduces algorithm complexity thereby reducing required processor power and hardware costs.

Another consideration in certain tissue treatments using electrosurgical methods has to do with arcing between instrument jaws. Arcing may be caused by high peak voltage and tends to have a negative impact on electrosurgical performance. Sinusoidal waveforms have a higher peak voltage compared to square waves with the same RMS value. For example, consider a waveform having a 100V RMS value. For a square wave output, the peak voltage would equal the RMS voltage so the peak value would be 100V. However, for a pure sinusoidal waveform, the peak voltage is equal to 1.414 times the RMS value so the peak voltage would be 141.4V. This discrepancy increases with the crest factor of the sinusoidal waveform, Accordingly, the lower peak voltage of the square wave output reduces the risk of arcing and improves performance of the electrosurgical device.

While several embodiments of the disclosure have been shown in the drawings and/or discussed herein, it is not intended that the disclosure be limited thereto, as it is intended that the disclosure be as broad in scope as the art will allow and that the specification be read likewise, Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. A square wave generator suitable for use with an electrosurgical device, the square wave generator comprising:
    a waveform synthesizer configured to generate a waveform;
    an amplifier operatively coupled to the waveform synthesizer for providing electrosurgical energy in a shape of square waves directly to tissue;
    at least one sensor configured to sense an operational parameter of the electrosurgical energy outputted from the amplifier and to provide a sensor signal corresponding thereto; and
    a controller adapted to receive the sensor signal and in response thereto control the waveform synthesizer.

2. The square wave generator according to claim 1, further comprising:
    a positive high voltage direct current source coupled to the amplifier; and
    a negative high voltage direct current source coupled to the amplifier,
    wherein the controller controls the output of the positive high voltage direct current source and the negative high voltage direct current source in response to the at least one sensor signal to control the output of the square wave generator.

3. The square wave generator according to claim 1, wherein the operational parameter is peak voltage.

4. The square wave generator according to claim 1, wherein the operational parameter is current.

5. The square wave generator according to claim 1, wherein the amplifier comprises at least two gain elements arranged in a push-pull configuration.

6. The square wave generator according to claim 5, wherein the at least two gain elements are selected from the group consisting of bipolar transistors, field-effect transistors, and laterally diffused metal oxide semiconductors.

7. The square wave generator according to claim 1 further comprising a gain stage coupled between the waveform synthesizer and the amplifier.

8. The square wave generator according to claim 7, wherein the gain stage further comprises a transformer.

9. The square wave generator according to claim 7, wherein the gain stage is configured to amplify the waveform from the waveform synthesizer and output the amplified waveform to the amplifier.

* * * * *